United States Patent
Mainx et al.

(10) Patent No.: US 8,658,130 B2
(45) Date of Patent: Feb. 25, 2014

(54) AGRICULTURAL COMPOSITIONS

(75) Inventors: Hans-Georg Mainx, Leichlingen (DE); Peter Hofer, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/201,249

(22) PCT Filed: Feb. 4, 2010

(86) PCT No.: PCT/EP2010/000670
§ 371 (c)(1), (2), (4) Date: Aug. 12, 2011

(87) PCT Pub. No.: WO2010/091817
PCT Pub. Date: Aug. 19, 2010

(65) Prior Publication Data
US 2011/0294667 A1    Dec. 1, 2011

(30) Foreign Application Priority Data

Feb. 13, 2009  (EP) ..................................... 09002015

(51) Int. Cl.
*A61K 36/14* (2006.01)
*A61K 51/00* (2006.01)

(52) U.S. Cl.
USPC .......................................... 424/1.73; 514/23

(58) Field of Classification Search
USPC ........................................... 424/1.73; 514/23
See application file for complete search history.

(56) References Cited

U.S. PATENT DOCUMENTS

| 6,103,770 A | 8/2000 | Trouve |
| 6,764,979 B2 | 7/2004 | Wollenweber et al. |
| 7,585,830 B2 | 9/2009 | Behler et al. |
| 2002/0009437 A1 | 1/2002 | Hiromoto |
| 2007/0161536 A1 * | 7/2007 | Behler et al. .................. 510/470 |

FOREIGN PATENT DOCUMENTS

| CA | 2396051 | 7/2001 | |
| DE | 268147 | 5/1989 | |
| DE | 10000320 | 7/2001 | |
| DE | 10018159 | 10/2001 | |
| DE | EP 2439187 | * 12/2008 | ............. C07C 67/03 |
| EP | 0804241 | 11/1997 | |
| EP | 1063883 | 10/2002 | |
| EP | 2072523 | 6/2009 | |
| WO | WO-98/09518 | 3/1998 | |
| WO | WO-2004/080177 | 9/2004 | |
| WO | WO-2005/087785 | 9/2005 | |

OTHER PUBLICATIONS

"EP Search Report for Appln. No. EP09002015.7", Aug. 26, 2009, 2 pages.
"PCT International Search Report for Appln. No. PCT/EP2010/000670", May 17, 2011, 4 pages.
EP Search Report and Opinion for Appln. No. EP09002015.7, Aug. 17, 2009, 4 pages.

* cited by examiner

*Primary Examiner* — Rebecca Prouty
*Assistant Examiner* — Danielle Sullivan
(74) *Attorney, Agent, or Firm* — Servilla Whitney LLC

(57) ABSTRACT

Suggested are agrochemical compositions, comprising (a) biocides, and (b) alkoxylation products of di- and/or oligosaccharide esters.

11 Claims, 2 Drawing Sheets

AGRICULTURAL COMPOSITIONS

CROSS-REFERENCE TO RELATED APPLICATIONS

This application is the National Stage entry of PCT/EP2010/000670, filed on Feb. 4, 2010, which claims priority to European Patent application number 09002015.7 filed on Feb. 13, 2009, both of which are incorporated herein by reference in their entireties.

FIELD OF THE INVENTION

The present invention is related to the area of additives for agriculture and concerns more particularly agricultural compositions comprising a new class of highly lipophilic carbohydrate additives.

BACKGROUND OF THE INVENTION

The crop protection market represents a total value of around €22 billion/year. Most biocides are formulated with adjuvants (also known as potentiators) to maximise their efficacy by fulfilling several functions. An adjuvant must provide good wetting of the leaf surface, facilitate the foliar penetration of the biocide under a wide range of climatic conditions and enhance, or at least not inhibit, translocation of the biocide, in particular the herbicide into the plant. In addition, it must not produce phytotoxic effects when used on specific resistant crops.

The use of ethoxylated vegetable oils as additives for biocide and plant protection formulations represents a well known state of the art. One of the first references describing ethoxylated triglycerides for this purpose has been a laid-open publication from earlier German Democratic Republic DD 268147 A1. In this context also reference is made to international patent application WO 98/009518 A1 (Cognis) disclosing agricultural composition comprising a liquid carrier and an emulsifier mixture consisting of alkyl polyglucosides and fatty acids. From the two German applications DE 100 00 320 A1 and DE 100 18 159 A1 (both Cognis) compositions are known comprising certain contact herbicides and ethoxylated fatty alcohols or fatty acids. European patent EP 0804241 B1 (SEPPIC) refers to ethoxylated fatty acid esters and triglycerides and their use as auto-emulsifiable systems for making agricultural compositions. Ethoxylated polyol esters are widely used in the formulation of pesticides. Well known are ethoxylated glycerides like ethoxylates of castor oil or soybean oil, or sorbitol- and sorbitan esters, which can be found in the market. EP 1063883 B1 (Cognis) describes the use of alkoxylation products of alkyl glycosides as adjuvants for agricultural compositions.

Although various types of biocides and also a huge number of additives, like adjuvants, emulsifiers, solubilisers and the like are available in the market, there is constant desire to develop new low viscous solvents and/or emulsifiers with improved low temperature stability, better colour and odour, higher compatibility with polar and non-polar solvents, while at the same time exhibiting a high degree of biodegradability and environmental friendliness. It has been the object of the present invention to comply with these needs of the market.

SUMMARY OF THE INVENTION

One aspect of the invention relates to an agrochemical composition comprising one or more biocides, and one or more alkoxylation products of di- and/or oligosaccharide esters. Methods of producing agrochemical compositions are also provided where an alkoxylation product of di- and/or oligosaccharide esters can be used as a solvent, an emulsifier, and/or an adjuvant. Methods of producing compositions can comprise using an alkoxylation product of di- and/or oligosaccharide esters as a tank-mix additive and/or a carrier medium for suspension concentrates or oil dispersions (SC or OD-formulations).

DETAILED DESCRIPTION OF THE INVENTION

Figure 1:
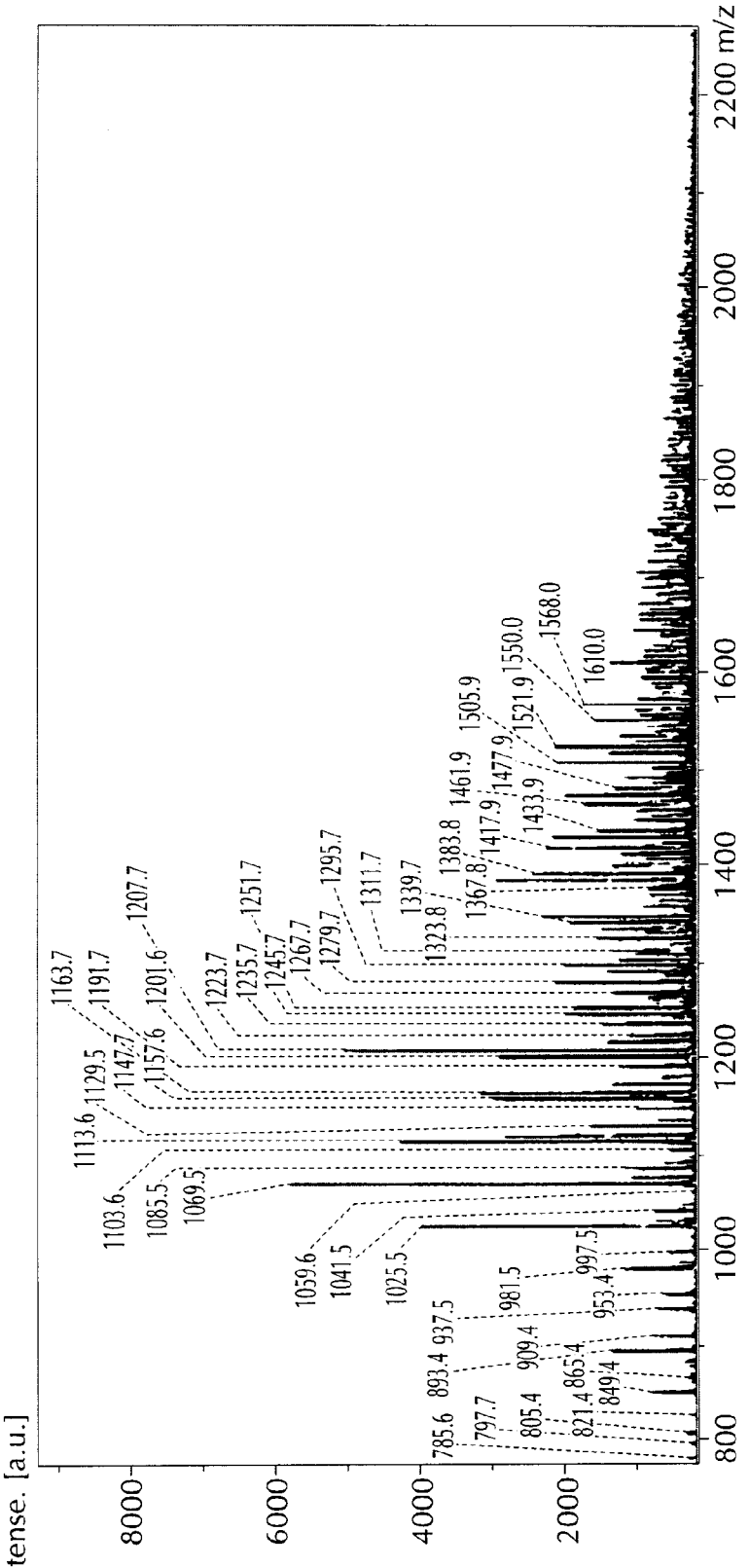
FIG. 1 is a MALDI spectrum of the product according to Example 1.

The present invention refers to agrochemical compositions, comprising
(a) biocides, and
(b) alkoxylation products of di- and/or oligosaccharide esters.

Surprisingly it has been observed that the compositions according to the invention exhibit lower viscosity, better colour, reduced odour and improved low temperature stability compared to similar biocide compositions based on other additives. Another advantage concerns the improved compatibility of the compositions with water and a wide range of solvents and carrier oils, which makes it possible to prepare all kinds of biocide formulations, like SL, EC, EW, SC, SE and OD. In addition the products are fully biodegradable and do not show any eco-toxicity.

Biocides

A biocide (component a) in the context of the present invention is a plant protection agent, more particular a chemical substance capable of killing different forms of living organisms used in fields such as medicine, agriculture, forestry, and mosquito control. Also counted under the group of biocides are so-called plant growth regulators. Usually, biocides are divided into two sub-groups:

pesticides, which includes fungicides, herbicides, insecticides, algicides, moluscicides, miticides and rodenticides, and antimicrobials, which includes germicides, antibiotics, anti-bacterials, anti-virals, anti-fungals, anti-protozoals and anti-parasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides.

A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following species: (3-ethoxypropyl)mercury bromide, 2-methoxyethylmercury chloride, 2-phenylphenol, 8-hydroxyquinoline sulfate, 8-phenylmercurioxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulfide, benalaxyl, benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothalisopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Herbicides.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are non-selective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing various chemical classes can be used, here specific reference is made to the The Pesticide Manual, Fourteenth edition, ed. CDS Tomlin, BCPC 2006. The following selection illustrates examples, which are by no means limitation to this invention: aryloxycarboxylic acid e.g. MCPA, aryloxyphenoxypropionates e.g. clodinafop, cyclohexanedione oximes e.g. sethoxydim, dinitroanilines e.g. trifluralin, diphenyl ethers e.g. oxyfluorfen, hydroxybenzonitriles e.g. bromoxynil, sulfonyureas e.g. nicosulfuron, triazolopyrimidines e.g. penoxsulam, triketiones e.g. mesotriones, ureas e.g. diuron. In the following, a number of specifically suitable herbicides are compiled:

- 2,4-D, a broadleaf herbicide in the phenoxy group used in turf and in no-till field crop production. Now mainly used in a blend with other herbicides that act as synergists, it is the most widely used herbicide in the world, third most commonly used in the United States. It is an example of synthetic auxin (plant hormone).
- Atrazine, a triazine herbicide used in corn and sorghum for control of broadleaf weeds and grasses. It is still used because of its low cost and because it works as synergist when used with other herbicides, it is a photosystem II inhibitor.
- Dicamba as benzoic acid, a persistent broadleaf herbicide active in the soil, used on turf and field corn. It is another example of synthetic auxin.
- Glyphosate, a systemic nonselective (it kills any type of plant) herbicide used in no-till burndown and for weed control in crops that are genetically modified to resist its effects. It is an example of a EPSPs inhibitor.
- Imazapic as imidazolinone, a selective herbicide for both the pre- and post-emergent control of some annual and perennial grasses and some broadleaf weeds. Imazapic kills plants by inhibiting the production of branched chain amino acids (valine, leucine, and isoleucine), which are necessary for protein synthesis and cell growth.
- Metolachlor as chloroacetamide, a pre-emergent herbicide widely used for control of annual grasses in corn and sorghum; it has largely replaced atrazine for these uses.
- Paraquat as bypyridylium, a nonselective contact herbicide used for no-till burndown and in aerial destruction of marijuana and coca plantings. More acutely toxic to people than any other herbicide in widespread commercial use.
- Picloram, clopyralid, and triclopyr as pyridinecarboxylic acids or synthetic auxins, used to control unwanted woody plants and broad-leaved weeds.

Insecticides.

An insecticide is a pesticide used against insects in all developmental forms. They include ovicides and larvicides used against the eggs and larvae of insects. Insecticides are used in agriculture, medicine, industry and the household. In the following, suitable insecticides are mentioned:

- Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex and their mixtures;
- Organophosphorus compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Methyl-parathion, Mevinphos, Naled, Omethoate, Oxydemetonmethyl, Parathion, Phorate, Phosalone, Phosmet, Phostebupirim, Pirimiphosmethyl, Profenofos, Terbufos, Tetrachlorvinphos, Tribufos, Trichlorfon and their mixture;
- Carbamates such as, for example, Aldicarb, Carbofuran, Carbaryl, Methomyl, 2-(1-Methylpropyl)phenyl methylcarbamate and their mixtures;
- Pyrethroids such as, for example, Allethrin, Bifenthrin, Deltamethrin, Permethrin, Resmethrin, Sumithrin, Tetramethrin, Tralomethrin, Transfluthrin and their mixtures;
- Plant toxin derived compounds such as, for example, Derris (rotenone), Pyrethrum, Neem (Azadirachtin), Nicotine, Caffeine and their mixtures.
- Neonicotinoids such as imidacloprid.
- Abamectin e.g. emamactin
- Oxadiazines such as indoxacarb
- Anthranilic diamides such as rynaxypyr Rodenticides.

Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorphacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e. g., warfarin 0.025-0.05%+cholecalciferol 0.01%. In some countries there are even fixed three-component rodenticides, i.e. anticoagulant+antibiotic+vitamin D, e. g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia.

Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970s, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e. g. Quintox®, containing 0.075% cholecalciferol) alone, or a combination of calciferol 0.01-0.075% with an anticoagulant are marketed.

Miticides, Moluscicides and Nematicides.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloro-isocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH<1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e. g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole.

The preferred biocides are selected from the group consisting of insecticides, herbicides or fungicides, namely oxyfluorfen, glyphosate, tebucanozol, desmedipham, phenmedipham, ethofumesat and their mixtures.

Alkoxylation Products of Di- and/or Oligosaccharide Esters

Many alkoxylation products of di-/and or oligosaccharide esters (component b) are generically known from the prior art. In a first embodiment of the invention said alkoxylation products may represent adducts of ethylene oxide and/or propylene oxide to esters of di- and/or oligosaccharides selected from the group consisting of disaccharides, trisaccharides and oligosaccharides having at least 4 and on average not more than 20 sugar units. The saccharides may represent oligoglucosides or oligofructoside or even mixtures of both structures. Preferred examples are selected from the group comprising saccharose, maltose, and maltotriose. For economic reasons suitable candidates can also be obtained by chemical or enzymatic degradation of polysaccharides like for example celluloses, starches or waste material from sugar industry. Also certain natural or synthetic gums or their degradation products, like for example xanthan gum are useful.

In a second embodiment of the invention said alkoxylation products may represent adducts of on average 1 to about 100, preferably about 5 to about 70 and more preferably about 10 to about 50 mol ethylene oxide and/or 1 to about 100, preferably about 20 to about 20 and more preferably about 5 to about 10 mol propylene oxide to esters of di- and/or oligosaccharides. Rather suitable products encompass products of on average 10 to 50 mol ethylene oxide and 5 to 10 mol propylene oxide. The distribution of the units may be randomized or blockwise.

In another embodiment of the invention said alkoxylation products may represent adducts of ethylene oxide and/or propylene oxide to $C_6$-$C_{22}$ fatty acid esters of di- and/or oligosaccharides. The fatty acid group may be derived from capronic acid, caprylic acid, caprinic acid, lauric acid, myristic acid, palmitic acid, palmoleic acid, stearic acid, isostearic acid, oleic acid, elaidinic acid, linoic acid, linolenic acid, 12-hydroxy stearic acid, ricinoleic acid, gadoleic acid, arachidonic acid, behenic acid, Erucic acid and their technical mixtures, like for example coco fatty acid, palm fatty acid, tallow fatty acid, sunflower fatty acid, soy fatty acid and the like. It is particularly preferred to use $C_8$-$C_{10}$ fatty acids or oleic acid for the preparation of the esters. The degree of esterification depends on the number of free hydroxyl groups in the carbohydrate body. Usually the degree will be about 0.1 to about 6, preferably about 1.5 to 4. For saccharose, for example the preferred degree of esterification is about 4.

Particular preferred are alkoxylation products representing adducts of on average 10 to 50 mol ethylene oxide and/or 1 to 10 mol propylene oxide to saturated or unsaturated $C_8$-$C_{18}$ esters of saccharose, namely the species saccharose+10EO octanoate/decanoate or saccharose+40EO+6PO tetraoleate.

Manufacturing of the Alkoxylation Products

It should be noted that the introduction of fatty acids by esterification leads to the decomposition of the basic structure of the saccharides. The preferred way for manufacturing the alkoxylation products is to subject the alkoxylated saccharides to transesterification with fatty acid alkyl esters. Unfortunately, conventional transesterification catalysts, like for example sodium methylate, usually lead to unwanted caramelisation reactions and to products showing a dark brownish colour.

Therefore, a preferred embodiment of the present invention refers to an improved process for making the alkoxylated di- and/or oligosaccharide esters using reducing mineral or organic acids as transesterification catalysts, which are selected from the group consisting of
  (i) sulphuric or sulphonic acids with an oxidation value of sulphur of less than 6 or their salts, and/or
  (ii) phosphoric or phosphonic acids with an oxidation value of phosphor of less than 5 or their salts.

Surprisingly it has been observed that using the catalysts the transesterification reaction can be conducted under milder conditions, in particular lower temperatures and neutral pH value, allowing to produce light coloured esters without unwanted odours. Another advantage is that the esters are free of traces of heavy metal catalysts like for example tin. Typical examples for reducing mineral or organic are sulphuric or sulphonic acids selected from the group consisting of sulphurous acid, dithionic acid, sulphinic acid and organic sulphinic acids and their alkali or alkaline earth salts. It is also possible to apply mineral or organic acids represent phosphorous or phosphonic acids selected from the group consisting of phosphorous acid, diphosphorous acid, hypophosphorous acid, and hypodiphosphorous acid or their alkaline or alkaline earth salts. Preferred salts are potassium salts.

Typically, the alkoxylated saccharides are mixed with carboxylic acid esters, preferred esters with low boiling alcohol components and highly preferred methyl esters and about 2% b.w. of a 25% b.w. solution of for example potassium hypophosphite in methanol. The mixture is set under a vacuum of about 300 mbar and heated up slowly under stirring to about 150 to about 220° C. After the removal of the water the reaction starts vigorously at a temperature of about 140 to about 150° C. After the removal of the first large amount of alcohol the vacuum is slowly reduced to less than 1 mbar and the reaction mixture is kept under these conditions for another 3 to 4 hours. Once the reaction is completed the final ester is cooled down and can be used without any additional purification. Usually, a mixture of mono- and oligoesters is obtained containing some unreacted saccharide alkoxylates as well. The remaining content of methyl esters is far below 1% b.w.

Industrial Application

Agricultural Compositions

In a preferred embodiment the agricultural compositions according to the present invention comprise:
  (a) about 10 to about 50% b.w., preferably about 15 to about 35% b.w. biocides:
  (b) about 1 to about 20% b.w., preferably about 5 to about 15% b.w. alkoxylation products of di- and/or oligosaccharide esters, and
  (c) 0 to about 80% b.w., preferably about 10 to about 70% b.w. auxiliary agents on condition that the amounts add with water up to 100% b.w.

Auxiliary Agents

Agricultural compositions may comprise as optional component (c) auxiliary agents, like solvents, emulsifiers, dispersants, adjuvants, and the like selected from the group consisting of fatty acid dialkyl amides, fatty acids, fatty alcohols, fatty alcohol polyglycolethers, end-capped fatty alcohol polyglycol ethers, and alkoxylated vegetable oils. Suitable auxiliaries may also be chosen from anionic components like alkyl benzene sulfonates, in particular dodecyl benzenesulfonates for example in form of their sodium, ammonium, triethanolammonium, or calcium salts, alkyl sulfates and/or alkyl ethersulfates in form of their sodium, ammonium or triethanolamine salts, or citric acid esters from fatty alcohol alkoxylates or fatty acid monoglycerides, or phosphoric acid esters of linear or branched fatty alcohols and/or their alkoxylated products in form of their potassium, ammonium or triethanolammonium salts.

Further on, additional embodiments of the present invention cover the use of alkoxylation products of di- and/or oligosaccharide esters as
  solvents for making agricultural compositions.
  emulsifiers for making agricultural compositions.
  adjuvants for making agricultural compositions.
  tank-mix additives.
  carrier medium for suspension concentrates or oil dispersions (SC or OD-formulations)

EXAMPLES

Example 1

475 g (440 g active, 0.36 mol) of an adduct of 20 moles ethylene oxide to saccharose were mixed with 276 g (1.1 mol) tallow fatty acid methyl ester (Edenor® Me C12-18, Cognis GmbH) and 15 g of a 25% solution of potassium hypophosphite. The mixture was set under a 300 mbar vacuum and heated up slowly under stirring to 180° C. After the removal of the water the reaction started vigorously at a temperature of about 140 to 150° C. After the removal of the first large amount of methanol the vacuum was slowly reduced to less than 1 mbar and the reaction mixture kept under these conditions for another 3 to 4 hours. Once the reaction was completed the ester was cooled down without any additional purification.

Yield: approx. 670 g Ester
Appearance: clear yellowish liquid with a fatty smell
pH-value: 6.2
The MALDI spectrum of the product is given in FIG. 1.

Example 2

506 g (471 g active, 0.4 mol) of an adduct of 20 mol ethylene oxide to saccharose were mixed with 129 g (0.4 mol)

sunflower methyl ester (Edenor® Me SV, Cognis GmbH) and 15 g of a 25% solution of potassium hypophosphite. The mixture was set under a 300 mbar vacuum and heated up slowly under stirring to 180° C. After the removal of the water the reaction started vigorously at a temperature of about 140 to 150° C. After the removal of the first large amount of methanol the vacuum was slowly reduced to less than 1 mbar and the reaction mixture kept under these conditions for another 3 to 4 hours. Once the reaction was completed the ester was cooled down without any additional purification.

Yield: approx. 580 g Ester

Appearance: clear yellowish liquid with a fatty smell pH-value: 7.4

Figure 2:
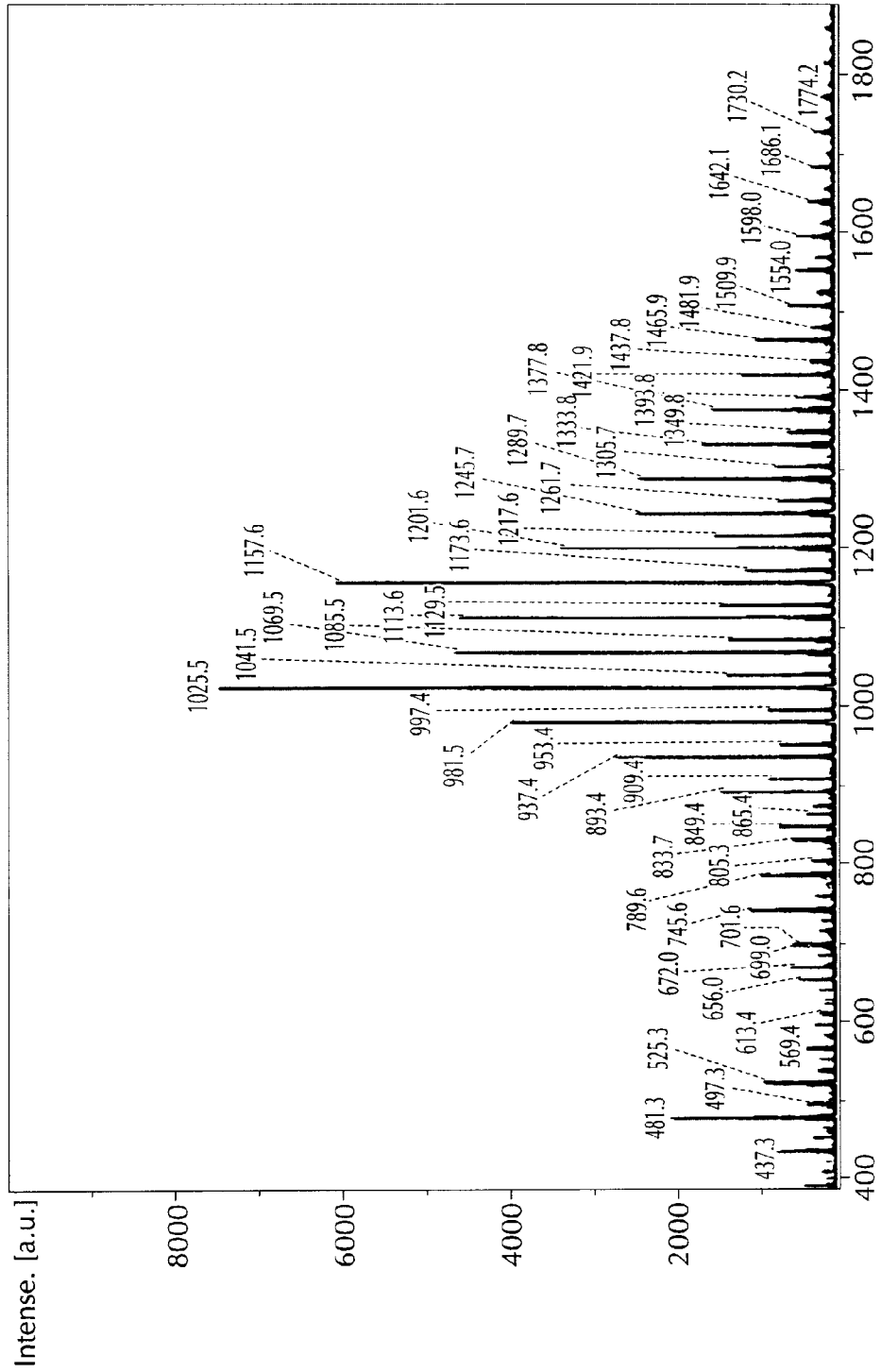
FIG. 2 is a MALDI spectrum of the product according to Example 2.

The MALDI spectrum of the product is given in FIG. 2.

Example 3

EC-Formulation of Oxyfluorfen

In the following Table 1 a composition of an EC-formulation comprising oxyfluorfen is given. The formulation represents a clear liquid and a 5% b.w. emulsion in water is stable over a minimum of 24 hours without any tendency for crystallisation.

TABLE 1

| EC formulation (amounts in % by weight) | |
| --- | --- |
| Oxyfluorfen | 27.0 |
| Agnique AMD 810 | 63.0 |
| Agnique ABS 65 C 4 | 6.0 |
| Dowanol DPM | 2.0 |
| Saccharose + 40EO + 6PO tetraoleate | 2.0 |

Example 4

SL-Formulation of Glyphosate

In the following Table 2 a composition of an SL-formulation comprising glyphosate is given. The formulation represents a clear liquid and a 5% b.w. emulsion in water is stable over a minimum of 24 hours without any tendency for crystallisation.

TABLE 2

| SL formulation (amounts in % by weight) | |
| --- | --- |
| Glyphosate IPA-salt | 36.0 |
| Saccharose + 10EO octanoate/decanoate | 15.0 |
| Water | Ad to 100 |

Example 5

EC-Formulation of Tebucanozole

In the following Table 3 a composition of an EC-formulation comprising glyphosate is given. The formulation represents a clear liquid and a 5% b.w. emulsion in water is stable over a minimum of 3 hours without any tendency for crystallisation.

TABLE 3

| EC formulation (amounts in % by weight) | |
| --- | --- |
| Tebuconazol techn. | 20.0 |
| Saccharose + 40EO tetraoleate | 10.0 |
| Fatty acid dimethylamide blend | 70.0 |

Example 6

EC-Formulation of an Herbicide Blend

In the following Table 4 a composition of an EC-formulation comprising glyphosate is given. The formulation represents a clear liquid and a 5% b.w. emulsion in water is stable over a minimum of 24 hours without any tendency for crystallisation.

TABLE 4

| EC formulation (amounts in % by weight) | |
| --- | --- |
| Desmedipham + Phenmedipham + Ethofumesat | 27.0 |
| Agnique ® AMD 10 | 35.0 |
| Agnique ® ME 610 | 18.0 |
| Agnique ® ABS 65 C 4 | 6.0 |
| Dowanol ® DPM | 2.0 |
| Saccharose + 40EO + 6PO tetraoleate | 2.0 |

What is claimed is:

1. An agrochemical composition comprising
    (a) one or more biocides, and
    (b) one or more esterified alkoxylation products of di- and/or oligosaccharides comprising C6-C22 fatty acid esters of adducts of ethylene oxide and/or propylene oxide to di- and/or oligosaccharides.

2. The composition according to claim 1, wherein said one or more biocides (component a) are selected from the group consisting of insecticides, herbicides, and or fungicides.

3. The composition according to claim 1 wherein said one or more biocides (component a) are selected from the group consisting of oxyfluorfen, glyphosate, tebucanozol, desmedipham, phenmedipham, ethofumesat and their mixtures.

4. The composition according to claim 1 wherein said one or more alkoxylation products (component b) comprise adducts of ethylene oxide and/or propylene oxide to esters of di- and/or oligosaccharides selected from the group consisting of saccharose, maltose, maltotriose, and degradation products of celluloses, starches or waste material from sugar industry.

5. The composition according to claim 1 wherein said one or more alkoxylation products (component b) comprise adducts of on average 1 to 100 mol ethylene oxide and/or 1 to 100 mol propylene oxide to esters of di- and/or oligosaccharides.

6. The composition according to claim 1 wherein said one or more alkoxylation products (component b) comprise adducts of on average 10 to 50 mol ethylene oxide and/or 1 to 10 mol propylene oxide to saturated or unsaturated C8-C18 esters of saccharose.

7. The composition according to claim 1 wherein said one or more alkoxylation products (Component b) comprise saccharose +10EO octanoate/decanoate or saccharose+40EO+ 6PO tetraoleate.

8. The composition according to claim 1 comprising:
    (a) 10 to 50% b.w. biocides,
    (b) 1 to 20% b.w. alkoxylation products of di- and/or oligosaccharide esters, and (c) 0 to 80% b.w. auxiliary agents,
on condition that the amounts add with water up to 100% b.w.

9. The composition according to claim 1 further comprising as component (c) one or more auxiliary agents selected from the group consisting of fatty acid dialkyl amides, fatty acids, fatty alcohols, fatty alcohol polyglycolethers, end-capped fatty alcohol polyglycol ethers, and alkoxylated vegetable oils, alkyl benzenesulfonates, alkyl sulfates, alkyl ether sulfates, citric acid esters of ethoxylated fatty alcohols and fatty acid monoglycerides.

10. A method of producing agrochemical compositions, the method comprising providing an alkoxylation product of di- and/or oligosaccharide esters comprising adducts of ethylene oxide and/or propylene oxide to C6-C22 fatty acid esters of di- and/or oligosaccharides and mixing the adducts of ethylene oxide and/or propylene oxide to C6-C22 fatty acid esters of di- and/or oligosaccharides with one or more biocides to form the agricultural composition of claim 1, wherein the alkoxylation product of di- and/or oligosaccharide esters is effective as a solvent, an emulsifier, an adjuvant, a tank-mix additive, and/or a carrier medium of the one or more biocides.

11. The agricultural composition of claim 1, wherein the one or more esterified alkoxylation products of di- and/or oligosaccharide esters are made by subjecting alkoxylated saccharides to transesterification with the C6-C22 fatty acid esters, where a transesterification catalyst is selected from the group consisting of: sulphuric or sulphonic acids with an oxidation value of sulphur of less than 6 or their salts, and phosphoric or phosphonic acids with an oxidation value of phosphor of less than 5 or their salts.

\* \* \* \* \*